United States Patent [19]

Olah

[11] 4,423,254

[45] Dec. 27, 1983

[54] SUPERACID CATALYZED PREPARATION OF RESORCINOL FROM META-ISOPROPYLPHENOL

[75] Inventor: George A. Olah, Beverly Hills, Calif.

[73] Assignee: PCUK Produits Chimiques Ugine Kuhlmann, Courbevoie, France

[21] Appl. No.: 383,941

[22] Filed: Jun. 1, 1982

Related U.S. Application Data

[60] Continuation-in-part of Ser. No. 211,772, Dec. 1, 1980, abandoned, which is a division of Ser. No. 130,402, Mar. 14, 1980, Pat. No. 4,339,614.

[51] Int. Cl.$^3$ .................... C07C 39/06; C07C 37/14
[52] U.S. Cl. .................... 568/781; 568/793; 568/743; 568/717
[58] Field of Search ............... 568/781, 793, 766, 763, 568/804, 743, 717

[56] References Cited

U.S. PATENT DOCUMENTS

| | | | |
|---|---|---|---|
| 2,008,337 | 7/1935 | Robinson et al. | 568/766 |
| 2,275,312 | 3/1942 | Tinkler et al. | 568/766 |
| 2,470,902 | 5/1949 | Rosenwald | 568/766 |
| 3,929,912 | 12/1975 | Herbert | 568/781 |
| 4,323,714 | 4/1982 | Malloy et al. | 568/804 |
| 4,339,613 | 7/1982 | Olah | 568/768 |
| 4,339,614 | 7/1982 | Olah | 568/768 |

FOREIGN PATENT DOCUMENTS 2071662 9/1981 United Kingdom ............... 568/763
2072172 9/1981 United Kingdom ............... 568/763

OTHER PUBLICATIONS

Olah et al., "J. Amer. Chem. Soc.", vol. 98: Apr. 8, 1976.
Olah, "Freidel–Crafts Chemistry", John Wiley & Sons, N.Y., (1973), pp. 367–371.
Olah et al., "Science, Reprint Series 5", Oct. 1979, vol. 206, pp. 13–20.

Primary Examiner—Werren B. Lone
Attorney, Agent, or Firm—Pennie & Edmonds

[57] ABSTRACT

Resorcinol is prepared by an improved process through superacid (such as perfluorinated alkanesulfonic superacids of one to eighteen carbon atoms or polymeric perfluorinated resinsulfonic acids, such as Nafion-H catalyzed cleavage-rearrangement reaction of meta-isopropylphenol hydroperoxide in the form of its protected ether or ester derivatives, including readily cleavable and reusable trimethylsilyl and trifluoromethanesulfonyl derivates. Part of the process is the preparation of needed meta-isopropylphenol in high purity free of other isomers by treating any mixture of isopropylphenol isomers in an excess of anhydrous hydrogen fluoride or a perfluorinated alkanesulfonic superacid of one to eighteen carbon atoms and a Lewis acid fluoride or by alkylating (transalkylating) phenol with a propyl alkylating agent in the presence of the aforementioned superacid systems.

5 Claims, No Drawings

SUPERACID CATALYZED PREPARATION OF RESORCINOL FROM META-ISOPROPYLPHENOL

This application is a continuation-in-part of application Ser. No. 211,772 filed Dec. 1, 1980, abandoned which is in turn a division of Ser. No. 130,402 filed Mar. 14, 1980, now U.S. Pat. No. 4,339,614.

TECHNICAL FIELD

Preparation of resorcinol by an improved process through superacid (such as perfluorinated alkanesulfonic superacids of one to eighteen carbon atoms or polymeric perfluorinated resinsulfonic acids, such as Nafion-H) catalyzed cleavage-rearrangement reaction of meta-isopropylphenol hydroperoxide in the form of its protected ether or ester derivatives, including readily cleavable and reusable trimethylsilyl and trifluoromethanesulfonyl derivates. Part of the process is the preparation of needed meta-isopropylphenol in high purity substantially free of other isomers by treating any mixture of isopropylphenol isomers in an excess of anhydrous hydrogen fluoride or a perfluorinated alkanesulfonic superacid of one to eighteen carbon atoms and a Lewis acid fluoride catalyst or by alkylating (transalkylating) phenol with a propyl alkylating agent in the presence of the aforementioned superacid systems.

BACKGROUND ART

Resorcinol (meta-dihydroxybenzene) is an industrial chemical of substantial significance. Its preparation is usually carried out through the high temperature (about 300° C.) alkali fusion of meta-benzenedisulfonic acid. For chemical, as well as environmental reasons, this process is disadvantageous. The Hock process of preparation of phenol was extended for the preparation of resorcinol through meta-diisopropylbenzene dihydroperoxide. However, the existence of two hydroperoxide groups simultaneously present in the intermediate dihydroperoxide can result in the formation of an increased number of by-products, particularly as the rate of the reaction is substantially slower than that of cumene. U.S. application Ser. No. 130,401 filed Mar. 14, 1980 describes ways to overcome some of these difficulties with the use of superacidic catalysts. Nevertheless, there is a practical need for improved preparation of resorcinol from readily available alternate starting materials, particularly phenol itself.

The only related approach, so far reported, is to be found in U.S. Pat. No. 3,028,410 (1962) describing the preparation of dihydroxybenzenes through sulfuric acid catalyzed decomposition-rearrangement (i.e. Hock-reaction) of the corresponding hydroperoxides. Inter alia, this patent describes examples of the preparation of resorcinol from meta-isopropylphenol in the form of its phosphate, acetate or methyl ether derivatives, by preparing the related hydroperoxides and their subsequent acid catalyzed conversion. The preparation of pure meta-isopropylphenol substantially free of other isomers, however, so far, was not possible and mixtures of the isomers are extremely difficult and costly to separate. Further, the Hock reaction of substituted isopropylbenzene hydroperoxides, can result in significantly increased number of by-products and low yields. Thus, no practical preparation of resorcinol from phenol, through meta-isopropylphenol was, until now, known.

SUMMARY OF THE INVENTION

The present invention is directed to an improved, efficient process for the preparation of resorcinol from phenol via superacid catalyzed cleavage-rearrangement of meta-isopropylphenol ethers or esters as well as highly improved methods for preparing the needed meta-isopropylphenol substantially free of any other isomer by isomerizing a mixture of isopropylphenol isomers with excess anhydrous hydrogen fluoride or a perfluorinated alkanesulfonic superacid of one to eighteen carbon atoms and a Lewis acid fluoride catalyst.

BEST MODES FOR CARRYING OUT THE INVENTION

It was discovered that meta-isopropylphenol hydroperoxide, in a form where the phenolic hydroxyl group is protected by a suitable ether or ester group (such as trimethylsilyl, trifluoromethanesulfonyl or trifluoroacetyl) prepared by known methods, such as the liquid phase oxidation of the protected meta-isopropylphenol esters or ethers with oxygen or air, can be cleanly and in high yield (about 90%) converted, via its Hock reaction, to resorcinol when treated with a superacidic catalyst, such as perfluorinated alkanesulfonic superacid catalyst of one to eighteen carbon atoms or a polymeric perfluorinated resinsulfonic acid, such as Nafion-H, and the like. The reaction is generally carried out in solvents, such as benzene, toluene, acetone, sulfolane, and the like, or preferentially mixtures thereof, at temperatures beteen about 20° and 200° C., preferentially between about 50° and 150° C., with generally 1 to 5% of the superacid catalyst dissolved or dispersed in the solvent system.

The polymeric perfluorinated resinsulfonic acids Nafion-H can be prepared from commercially available Nafion-K (DuPont) ion-membrane resin by acidification. This perfluorinated resinsulfonic acid comprises a fluorinated polymer having sulfonic acid groups in the amount of about 0.01 to 5 mequiv/gram catalyst. The polymer catalyst contains a repeating structure, which can be depicted as:

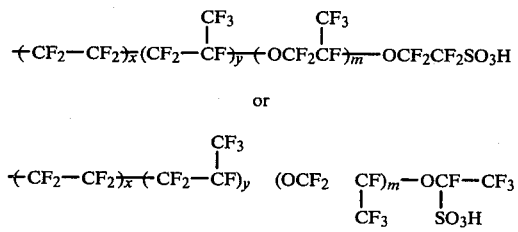

where the ratio of x over y varies from about 2 to about 50, and m is 1 or 2. This polymer structure is available commercially under the tradename Nafion resin from DuPont. Polymer catalysts of the above structure can be prepared in various ways. One method, disclosed in Conolly et al. U.S. Pat. No. 3,282,875 and Cavanaugh et al. U.S. Pat. No. 3,882,093 comprises polymerizing the corresponding perfluorinated vinyl compounds. It is also possible to prepare polymer catalyst according to U.S. Pat. No. 4,041,090 by copolymerizing the corresponding perfluorinated vinyl ethers with perfluoroethylene and/or perfluoroalpha-olefins. The specific fluorinated repeating structure depicted above is not critical but perfluorinated is preferred. The Nafion ion exchange resins can be acidified in various known manners such as set forth in Example 4 below.

Superacids are those acids having an acidity function below $H_o = -11$ on the logarithmic Hammett $H_o$ acidity function scale. For example, 100% sulfuric acid has an $H_o$ function of $-11$ while superacids would have $H_o$ values of $-14$, $-20$, etc.

The term "phenol protecting group" as used herein is well known. There are many known protective groups, particularly ether and ester groups, which will perform the protective function and which are also easily cleavable. The book by J. F. W. McOmie "Protective Groups in Organic Chemistry" Plenum Press, 1973 in Chapter 4 by E. Haslam discusses many of these known groups. Perfluorosulfonic or carboxylic acid ester protective groups are not included in this review since these are relatively new in their application. A recent monograph "Vinyl Cations" by Peter J. Stang, et al., Academic Press, 1979, Pg. 330, discusses fluorine substituted leaving groups and gives a table comparing various protecting groups for their effectiveness. Although the particular protecting group employed can be selected from the knowledge of the art, the best protecting groups found to data are trimethylsilyl, trifluoroalkanesulfonyl, particularly trifluoromethanesulfonyl and trifluoroacetyl.

It is a significant aspect of the invention to obtain the needed starting material, i.e., meta-isopropylphenol, in high isomeric purity. Methods known for preparation of this compound consist of isopropylation of phenol, giving isomeric mixtures with the ortho and para isomers predominating. Subsequent acid catalyzed isomerization, using usual Friedel-Crafts conditions in the liquid phase with catalyst, such as $AlCl_3$, $BF_3$, and the like, or over solid catalysts, such as Nafion-H and PDSA, gives an isomer distribution containing about 15% ortho, 65% meta and 20% para isomer, representing the thermodynamic equilibrium composition, but still necessitating difficult to achieve and expensive separation of the isomers which, due to their close boiling range, can generally not be achieved by simple distillation alone.

It has now been discovered that when isopropylphenols (ortho, para or any mixture of isomers), were treated in excess of anhydrous hydrogen fluoride with a Lewis acid fluoride, such as boron trifluoride, phosphorus pentafluoride, antimony pentafluoride, arsenic pentafluoride, tantalum pentafluoride, niobium pentafluoride, or with an excess of anhydrous hydrogen fluoride and a perfluorinated alkanesulfonic superacid of one to eighteen carbon atoms, and the like, at temperatures between $-50°$ and $200°$ C., preferentially between $75°$ and $130°$ C., substantially complete conversion to the meta-isomer takes place, accompanied by some disproportionation to phenol and diisopropylphenol. The amount of disproportionation can be substantially decreased when recycling di- or triisopropylphenols into the reaction mixture, effecting transisopropylation, and, thus, shifting the equilibria towards the desired meta-isopropylphenol. Indeed, when phenol is reacted under the superacidic reaction conditions with di- or triisopropylphenols, the only isomeric monoalkylate obtained is meta-isopropylphenol. In contrast, if transalkylation is carried out under usual Friedel-Crafts conditions, the products contain all three isomeric isopropylphenols, with the amount of the metaisomer ranging from 40 to 65%.

Superacid systems form protonated complexes, i.e., arenium ions with isopropylphenols, if which the one derived from the meta isomer is the most stable. Thus, the superacid systems tend to selectively extract the meta isomer and allow a selective conversion of all isomers into the meta product. Such isomerizations were known previously only for methylbenzenes (McCaulay and Lien, J. Am. Chem. Soc., 74, 6246 (1952)), but not for isopropylbenzenes or alkylphenols (including isopropylphenols). Whereas methylbenzenes isomerize intra-molecularly, isopropylbenzenes tend to isomerize by inter-molecular processes. Thus, no extrapolation is possible from methylbenzenes to isopropylbenzenes or isopropylphenols, which are also expected to significantly disproportionate.

The isopropylation of phenol with propylene, isopropyl halides (particularly fluoride, bromide and chloride) or isopropyl alcohol can also be carried out in the aforementioned superacidic systems with respect to the isomerization of para and ortho isopropylphenol, and results in the exclusive formation of meta-isopropylphenol.

Meta-isopropylphenol can also be obtained by carrying out the isopropylation of phenol by transalkylating with di- or triisopropylbenzenes or di- or triisopropylphenols in the same superacid systems.

The scope of the invention is further described in connection with the following examples, which are set forth for purposes of illustration only and are not to be construed as limiting the scope of the invention in any manner.

EXAMPLE 1

5 g of trifluoromethanesulfonic acid is dissolved in 100 ml of sulfolane and the solution heated to $50°$-$60°$ C. A solution of 17 g (0.1 mol) meta-isopropylphenol trifluoromethanesulfonate hydroperoxide, prepared by the liquid phase oxidation of meta-isopropylphenol trifluoromethanesulfonate, in 100 ml sulfolane is then slowly added to the stirred solution. After completion of the addition, the temperature is raised to $100°$ C. to complete the reaction while distilling off formed acetone. Resorcinol is isolated after complete hydrolysis of the ester either by extraction by a suitable solvent, such as isopropyl ether or is separated by vacuum distillation. Yield obtained 9.8 g (89%) with 94% purity.

EXAMPLE 2

Reaction is carried out as in Example 1, but using meta-isopropylphenol trimethylsilyl ether hydroperoxide. The silyl ether is prepared from meta-isopropylphenol and trimethylsilyl chloride. Yield of resorcinol is 91% purity. Trimethylsilanol obtained in the workup upon hydrolysis of the silyl ether can be easily reconverted to trimethylsilyl chloride and thus recycled.

EXAMPLE 3

Reaction is carried out as in Example 1, but with 5 g perfluorobutane-sulfonic acid as catalyst. The yield is 83% with 92% purity.

EXAMPLE 4

Reaction is carried out as in Example 1 but using Nafion-H as catalyst dispersed in 150 ml sulfolane and at a temperature of $130°$ to $150°$ C. Yield of resorcinol is 74% with 89% purity.

Nafion-H was prepared from commercially available (DuPont) potassium salt of the resin (Nafion-K) by acidification with 20 to 30% nitric acid, stirring at $20°$ to $50°$ C. for four hours, filtering the resin acid, washing it acid free with water and subsequently drying it in a vacuum oven at 150° to 110° for eight hours.

EXAMPLE 5

14 g (0.1 mol) of a mixture of isopropylphenols containing 70% ortho and 30% para isomers is dissolved in 150 ml of anhydrous hydrogen fluoride, placed into a stainless steel autoclave, saturated with boron trifluoride, and heated subsequently to 110° C. for six hours. After depressurizing and distilling off hydrogen fluoride and boron trifluoride, the mixture was washed with ice water, neutralized, washed again, dried and distilled. Gas liquid chromatographic analysis showed the isopropylphenol fraction, which comprises 61% of the product, to be practically pure (99%) meta isomer. Phenol and diisopropylphenols, formed by disproportionation, comprise the rest of the products.

EXAMPLE 6

9.4 g (0.1 mol) phenol and 18 g (0.05 mol) of diisopropylphenols are dissolved in 150 ml of anhydrous hydrogen fluoride at 20° C. and transferred to a 500 ml stainless steel pressure autoclave. The solution is saturated with boron trifluoride and subsequently is heated to 100° C. for four hours. After workup, as in Example 5, 41% of meta-isopropylphenol is obtained in 99% purity.

EXAMPLE 7

9.4 g (0.1 mol) phenol is dissolved in 100 ml of anhydrous hydrogen fluoride and while keeping the solution at about 0° C., 2 g (0.05 mol) propylene was introduced and stirring continued for 15 minutes. The reaction mixture is then saturated with boron trifluoride and heated to 100° C. for 30 minutes. After workup, 59% isopropylphenol is obtained, containing 99% meta isomer, together with 31% phenol and some diisopropylphenols.

While the invention has been described in connection with preferred embodiments, it is not intended to limit the invention to the particular forms set forth, but, on the contrary, it is intended to cover such alternatives, modifications, and equivalents as may be apparent to those skilled in the art.

I claim:
1. A process of preparing substantially pure meta-isopropylphenol which comprises propylating phenol with:
   (a) propylene,
   (b) an isopropyl halide,
   (c) an isopropyl alcohol,
   (d) di isopropylbenzene,
   (e) tri isopropylbenzene,
   (f) di isopropylphenol, or
   (g) tri isopropylphenol,
in the presence of a combination catalyst of:
   (1) an excess of anhydrous hydrogen fluoride and a Lewis acid fluoride, or
   (2) an excess of anhydrous hydrogen fluoride and a perfluorinated alkanesulfonic superacid of one to eighteen carbon atoms,
at a temperature sufficient to produce substantially pure meta-isopropylphenol.

2. The process of claim 1 in which the Lewis acid fluoride catalyst is boron trifluoride, phosphorous pentafluoride, arsenic pentafluoride, antimony pentafluoride, tantalum pentafluoride or niobium pentafluoride.

3. A process of preparing substantially pure meta-isopropylphenol which comprises reacting a mixture of phenol and diisopropylphenol in the presence of a combination catalyst of:
   (1) an excess of anhydrous hydrogen fluoride and a Lewis acid fluoride, or
   (2) a excess of anhydrous hydrogen fluoride and a perfluorinated alkanesulfonic superacid of one to eighteen carbon atoms,
at a temperature sufficient to produce substantially pure meta-isopropylphenol.

4. The process of claim 3 in which the Lewis acid fluoride catalyst is boron trifluoride, phosphorous pentafluoride, arsenic pentafluoride, antimony pentafluoride, tantalum pentafluoride or niobium pentafluoride.

5. The process of one of claims 1, 2, 3, or 4 carried out at temperatures between about −50° and 200° C.

* * * * *

UNITED STATES PATENT AND TRADEMARK OFFICE
CERTIFICATE OF CORRECTION

PATENT NO. : 4,423,254
DATED : December 27, 1983
INVENTOR(S) : George A. Olah

It is certified that error appears in the above—identified patent and that said Letters Patent is hereby corrected as shown below:

Column 2, line 51, second formula, reads "(OCF$_2$" should read --~(OCF$_2$~--

Column 3, line 24, reads "data" should read --date--

Column 5, line 2, reads "150°" should read --105°--.

Signed and Sealed this

Third Day of July 1984

[SEAL]

Attest:

GERALD J. MOSSINGHOFF

Attesting Officer

Commissioner of Patents and Trademarks